United States Patent [19]

Torossian et al.

[11] 4,014,909
[45] Mar. 29, 1977

[54] ESTERS OF 21-THIOL STEROIDS

[75] Inventors: Dieran Robert Torossian, Bourg-La-Reine; Gilbert Gustave Aubard, Palaiseau; Jacky Marcel Gerard Legeai, Antony, all of France

[73] Assignee: Jouveinal S.A., Cachan, France

[22] Filed: May 28, 1974

[21] Appl. No.: 473,388

[30] Foreign Application Priority Data

May 30, 1974 France .............................. 73.19734

[52] U.S. Cl. .......................... 260/397.45; 424/243
[51] Int. Cl.² .......................................... C07J 31/00
[58] Field of Search .......................... 260/397.45; /Machine searched steroids

[56] References Cited
UNITED STATES PATENTS

| | | | |
|---|---|---|---|
| 2,814,632 | 11/1957 | Nussbaum | 260/397.45 |
| 3,687,942 | 8/1972 | Annen | 260/239.55 |
| 3,803,133 | 4/1974 | Vogt | 260/239.55 |

FOREIGN PATENTS OR APPLICATIONS

| | | | |
|---|---|---|---|
| 1,187M | 3/1962 | France | 260/397.45 |
| 2,070,077 | 10/1971 | France | |

*Primary Examiner*—Ethel C. Love
*Attorney, Agent, or Firm*—Charles E. Baxley

[57] ABSTRACT

The present invention relates to new esters of the 21-thiol-steroids, having the general formula given at (I) below, and also to a method of preparation of these new esters:

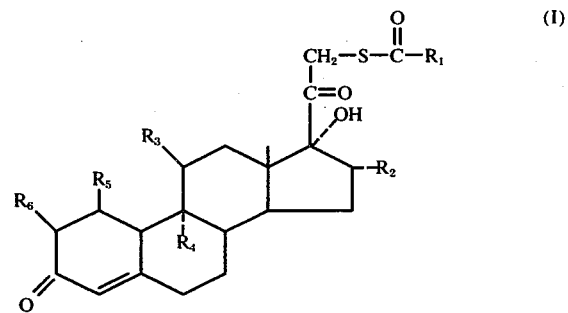

in which:
$R_1$ represents an alkyl radical comprising a number of carbon atoms between 4 and 9, or a para-fluoro-aryl radical;
$R_2$ represents an atom of hydrogen or a methyl radical;
$R_3$ represents a hydroxyl radical of a ketone function;
$R_4$ represents an atom of hydrogen or an atom of fluorine;
$R_5$ and $R_6$ each represent an atom of hydrogen or a second bond between the carbon atoms C–1 and C–2.

A method of preparation of the above new esters comprises the operation of condensation of:
Derivatives of the general formula below, in which $R_2$, $R_3$, $R_4$, $R_5$, $R_6$ have the same significations as above;
with alkaline salts of the S-thio-carboxylic acids belonging:
either to the group of thio-alkanoic acids comprising a number of carbon atoms between 5 and 10;
or to the group of halogen-benzene thio-carboxylic acids

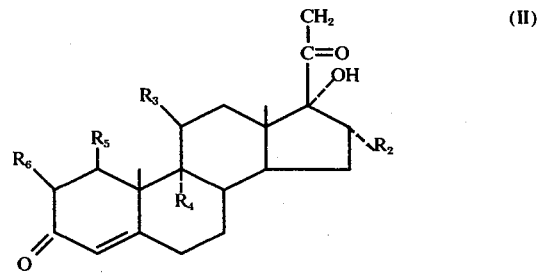

The esters of the invention have a considerable anti-inflammatory activity but also have small systemic effects and are applied especially to the local treatment of inflammatory illnesses.

4 Claims, No Drawings

ESTERS OF 21-THIOL STEROIDS

The present invention relates to new esters of the 21-thiol steroids having the general formula I

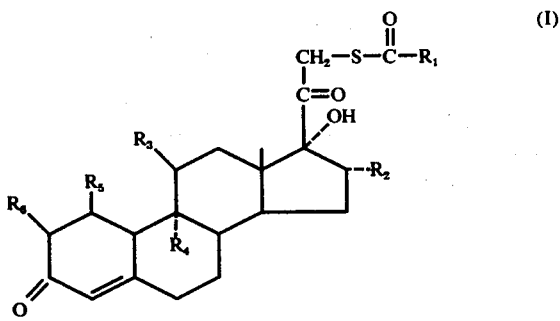

in which:
R₁ represents an alkyl radical comprising a number of carbon atoms equal to or greater than 4, preferably comprised between 4 and 9 atoms of carbon, or a parafluoro-aryl radical.

R₂ represents an atom of hydrogen or a methyl radical.

R₃ represents a hydroxyl radical or a ketone function.

R₄ represents an atom of hydrogen or an atom of fluorine.

R₅ and R₆ each represent an atom of hydrogen or a second bond between the carbon atoms C-1 and C-2.

Several publications describe the modification of the group 21-hydroxy-methyl of the corticoids, and more particularly the replacement of the oxygen of this function by sulphur.

Thus, the 21-thio-acetate of hydrocortisone is synthetized and declared free of all interesting biological activity (J. Org. Chem. 26,1233, 1961).

Other derivatives have been proposed as anti-inflammatory products having solely a systemic action on the system or a local action and a systemic action:

The 21-thio-acetate and 21-thio propionate of prednisolone (U.S. Pat. No. 2,814,632) have been described as possessing an adreno-corticoid activity accompanied by considerable diuretic activity.

The 21-thio-acetate of dexamethasone (French Pat. No. 1187 M) has been proposed as an anti-inflammatory product with a local action and a systemic action.

The therapeutic use of corticoids having a systemic action generally gives rise to harmful "secondary effects" (Presse Medicale No. 31,1419 – 1423, 1970).

These secondary effects comprise mainly: endocrine troubles, sodium retention accompanied by a leakage of potassium, weakening of the defense reactions of the organism, which result in a pro-infection effect, digestive ulcers and disturbances of the glucidic, proteic and lipidic metabolisms.

The number and the variety of these secondary effects necessitate a certain prudence and careful supervision during the use of these products.

The present invention has for its object to find a remedy for these disadvantages.

It has been found that, in a surprising manner, the structures forming the object of the present invention comprising a thio-alkanoic group of high molecular weight, possess a considerable anti-inflammatory activity but they have only small systemic effects. The therapeutic doses thus remain very remote from those capable of causing the appearance of the secondary effects previously described.

Thus, certain substances according to the invention possess a thymolytic activity 100 times less than that of the glyco-corticoid of reference, whereas conversely, their local anti-inflammatory activity is greater than that of the same reference.

Generally speaking, the substances forming the object of the present invention have shown a strongly reduced or nul activity on the glucidic and proteic metabolisms, little or no regression of the adrenal glands, no sodium retention.

In consequence, these substances are therapeutic agents having a very high safety in use, and this applies even in heavy doses, which find their application in the local treatment of inflammatory affections, such as the following:

Cutaneous illnesses and mucous illnesses that can be treated by cordicoids;

auto-rhino-laryngological and ophthalmological illnesses of an inflammatory and/or allergic nature;

low digestive inflammations such a colities, rectocolities, and recto-sigmoiditis;

collagen troubles, articular and thumatismal illnesses;

asthma, emphysema and respiratory fibrosis.

In addition, and contrary to the corresponding non-sulphurous steroids, these products have a long period of action free from "rebound effect" which is of great interest in the treatment of chronic inflammatory illnesses.

According to the invention, the new esters of the 21-thiol steroids are prepared by condensation between:

On the one hand iodized derivatives having the general formula II:

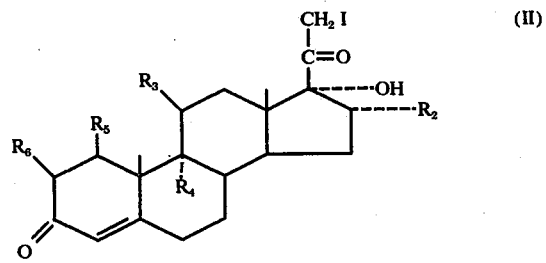

in which
R₂, R₃,R₄, R₅ and R₆ have the same signification as before;

On the other hand, S-thio-carboxylic acids utilized in their salified form, preferably in the form of the alkaline salts of these acids, especially the sodium salt.

As S-thio-carboxylic acids, there are employed acids such as:

The thio-alkanoic acids comprising a number of carbon atoms equal to or greater than 5 and perferably comprised between 5 and 10, especially the S-thio-pivalic acid and the S-heptanethioic acid;

the halogeno-benzene-thio-carboxylic acids, especially parafluoro-S-thio-benzoic acid.

In order to salify the S-thio-carboxylic acid, the procedure is preferably as follows:

The solvent is introduced into the reactor while stirring, preferably anhydrous acetone, and the S-thiocarboxylic acid.

Then the sodium is introduced, preferably in the form of a methanol solution of sodium methylate, which is added drop by drop.

The operating conditions of the process of condensation of the iodized derivatives of formula II and the alkaline S-thio-carboxylates are variable; however, the operation is generally carried out in the following manner:

There are introduced into a reactor comprising a reflux condenser, mechanical stirrer, the reaction solvent, especially anhydrous acetone, and then the iodized derivative of formule II; to the suspension or solution thus formed there is added the acetone solution of the alkaline salt of S-thio-carboxylic acid previously prepared. The reaction medium is brought up to reflux and the solvent is then eliminated by distillation under vacuum.

It must be noted however that it is also possible to effect the condensation by introducing the iodized dervatives of formula II in the powder form or in an acetone solution in the solution of sodium salt of S-thio-carboxylic acid and continuing the reaction as previously described.

The product obtained is purified depending on tne case, either directly by crystallization from an alcohol having a low molecular weight or by column chromatography followed by a crystallization from the appropriate solvent or mixed solvents.

The molar ratio between the alkaline S-thio carboxylate and the iodized derivative of formula II employed is comprised between 1.4 mol of alkaline salt per mol of iodized derivative and 14 mols of alkaline salt per mol of iodized derivative.

The reaction temperatures are determined in dependence on the nature of the solvent and are in principle comprised between 56° and 102° C.

The time of the condensation reaction is favorably comprised between half an hour and 8 hours and preferably between 1 hour and 3 hours. For these reaction periods and according to the reactants utilized, the yields are substantially comprised between 12.5 and 90%. Generally speaking, the time of the reaction is determined in such manner as to limit the formation of secondary derivatives.

In order to define the characteristics of the ester of the 21-thiol steroids thus prepared, analytic chemical methods are utilized, such as functional analysis and elementary centesimal analysis, and physico-chemical methods such as the ultra-violet and infra-red spectra.

The method which has just been described in general terms has been utilized for a whole variety of radicals $R_1$, $R_2$, $R_3$, $R_{R5}$, $R_6$; it will be seen in particular in connection with the non-limitative examples which follow below. These examples have been chosen in such manner as to define the utilization of the method according to the invention for at least one type of radical belonging to the families claimed hereinafter.

EXAMPLE 1

Dihydroxy-11$\beta$, 17$\alpha$Thiol 21 Dioxo-3,20 Pregnadiene-1,4 -21 Pivalate (JO 1007).

In a one liter three necked round bottomed flask equipped with a dropping funnel, a mechanical stirrer and a calcium chloride tube to protect the apparatus from moisture, there are introduced successively 400 cu.cm. of anhydrous acetone and 28.36 grams of S-thio-pivalic acid (0.24 mol.).

55.8 cu.cm. of a methanol solution of sodium methylate 3.58 M (0.2 mol) are introduced drop by drop in 12 minutes.

There is no modification of temperature, but the initial pale yellow colour becomes darker. After the introduction, stirring is continued for 5 minutes.

On the other hand, in a reactor of 10 liters fitted with a mechanical stirrer, a dropping funnel and a thermometer and a reflux condenser protected from moisture by a calcium chloride tube, there are introduced 6.4 liters of anhydrous acetone followed by 64 grams (0.136 mol) of dihydroxy-11$\beta$,17$\alpha$iodo-21 dioxo-3,20 pregnadiene-1,4.

To this suspension, the acetone solution of sodium S-thiopivalate prepared above is introduced while stirring in 30 minutes. There is no change in temperature, the medium turns yellow and the product dissolves gradually.

The solution is brought up to the acetone reflux for 2 hours and then the solvent is eliminated by distillation under vacuum. The yellow oily residue is poured into 1.2 liters of water, filtered and dried under vacuum at 40° C. The weight is 80 grams.

The product is purified by dissolving in 4 liters of boiling methanol and treatment of the solution with animal-charcoal.

After cooling, the very slightly yellow precipitate is filtered and dried under vacuum at 40° C.; weight 44.6 grams; yield 71.2%.

Analysis $C_{26}H_{36}O_5S$: calculated %: C, 67.80; H, 7.88; S, 6.96; found %: C, 67.84; H, 7.90; S, 6.79. Physical characteristics: F=238° C. $[\alpha]_D^{20}=+118°$, (dioxanne; c = 1%), $\lambda$max. (methanol) at 239.5 nm, log.$_{10}$ = 4.219; Main absorptions of infra-red spectrum - (KBr pellet): 1720, 1682, 1660, 1620, 1113, 895, 812 and 720 cm$^{-1}$

EXAMPLE 2

Dihydroxy-11$\beta$, 17$\alpha$thiol-21 dioxo-3,20 pregnadiene-1,4-21 heptanoate (JO 1009)

In a 100 cu.cm three necked round bottomed flask equipped as described in Example 1, there are introduced 50 cu.cm. of anhydrous acetone, 4.36 grams of S-heptane-thioic acid (0.03 mol) and finally 7.15 cu.cm of methanol solution of sodium methylate 3.5 M (0.025 mol).

On the other hand, in a 100 cu.cm. three necked round bottomed flask equipped as described in Example 1, there are introduced 800 cu.cm. of anhydrous acetone and 8 grams of dihydroxy-11$\beta$, 17$\alpha$ iodo-21 dioxo-3,20 pregnadiene-1,4 (0.017 mol).

The solution of sodium S-heptanethioate obtained above is introduced to the suspension and there is observed the gradual dissolving of the product. After 2 hours reflux, the solution is treated as in Example 1.

The residue is purified by recrystallization from 60 cu. cm. of methanol: weight = 4.85 grams; yield = 58%.

Analysis: $C_{28}H_{40}O_5S$: Calculated %: C, 68.82; H, 8.25; S, 6.56. found %: C, 68.71; H, 8.15; S, 6.61. Physical characteristics: F = 159° C $[\alpha]_D^{20} = +101°$, (dioxanne: c = 1.25%); $\lambda$max. (methanol) at 237.5 nm, log.$_{10}$ $\epsilon$ = 4.236; Main absorptions of infra-red spectrum - (KBr pellet): 1725, 1695, 1655, 1600, 1232, 1135, 1112, 895, 830 and 720 cm$^{-1}$.

EXAMPLE 3

Thiol-21 dioxo-3,20 pregnadiene-1,4-21 p.fluoro benzoate (JO. 1014)

Under the same conditions as in Example 2, starting frol 4.68 grams of S-p.fluoro-thio-benzoic acid (0.03 mom) and 6.85 cu. cm. of sodium methylate solution 3.66 M (0.025 mol) on the one hand and 8 grams of dihydroxy-11$\beta$, 17$\alpha$ iodo-21 dioxo-3,20 pregnadiene-1,4 (0.017 mol) on the other hand, there is obtained after treatment 9.8 grams of crude product which is purified by crystallization from 50 cu.cm. of methanol; weight: 4.55 grams; yield: 53.7%.

Analysis: $C_{28}H_{31}FO_5S$: calculated %: C, 67.45; H, 6.27; F, 3.81; S 6.43. found %: C, 67.33; H, 6.14; F, 3.63; S, 6.41. Physical characteristics: F: 240°–245° C. $[\alpha]_D^{20} = +150°$ (dioxanne, c = 0.3%); $\lambda$max. (methanol) at 233 nm log.$_{10}$ $\epsilon$ = 4.576; Main absorptions of infra-red spectrum - (KBr pellet): 1718, 1655, 1590, 1505, 1232, 1210, 1160, 1120, 920, 850, 720 and 620 cm$^{-1}$

EXAMPLE 4

Dihydroxy-11$\beta$, 17$\alpha$ thiol-21 dioxo-3,20 fluoro-9$\alpha$ methyl-16$\alpha$ pregnadiene-1,4-21-pivalate (JO 1008)

In a three necked round bottomed flask of one liter there is prepared sodium S-thio-pivalate as described in Example 1, starting with 10.35 grams of S-thiopivalic acid (87.6 mmols) and 27.3 cu.cm. of sodium methylate solution 3.21 M (87.6 mmols) in 150 cu.cm. of anhydrous acetone.

There is then introduced rapidly 3.4 grams of dihydroxy-11$\beta$, 17$\alpha$ iodo-21 dioxo-3,20 fluoro-9$\alpha$ methyl-16$\alpha$ pregnadiene-1,4 (6.76 mmols) in solution in 200 cu.cm. of anhydrous acetone.

After two hours at the reflux of the solvent, the reaction medium is treated as in Example 1. There are obtained 2.6 grams of crude product which are purified by crystallization (from methanol; weight: 2.39 grams; yield = 71.8%.

Analysis: $C_{27}H_{37}FO_5S$: Calculated %: C, 65.82; H, 7.57; F, 3.86; S, 6.51; Found %: C, 65.95; H, 7.63; F, 3.87; S, 6.59. Physical characteristics: F = 240°–245° C. $[\alpha]_D^{20} = 92°$, (dioxanne; g = 1%); $\lambda$max. (methanol) at 236.5 nm, log.$_{10}$ $\epsilon$ = 4.270; Main absorptions of infra-red spectrum (KBr pellet): 1715, 1660, 1610, 1455, 1140, 980, 950, 930, 900 and 710 cm$^{-1}$.

EXAMPLE 5

Dihydroxy611$\beta$, 17$\alpha$ thiol-21 dioxo-3,20 fluoro-9$\alpha$ methyl-16$\alpha$ pregnadiene-1,4-21 heptanoate (JO 1010)

The reaction is carried out as described in Example 4 starting with 12.81 grams of S-heptanethioic acid (87.6 mmols) on the one hand; and 3.4 grams of dihydroxy-11$\beta$, 17$\alpha$ iodo-21 dioxo-3,20 fluoro-9$\alpha$ methyl-16$\alpha$-pregnadiene-1,4 (6.76 mmols) on the other hand.

After reaction and evaporation of the acetone, the residue is treated with 800 cu.cm. of water and the suspension is extracted by three times 100 cu.cm. of chloroform. The combined organic phases are dried and there are obtained 4.6 grams of an oily residue after evaporation of the chloroform under vacuum.

The residue is first purified by column chromatography on 70 grams of Florisil 60 – 100 mesh. After the passage of hexane and then benzene, the elution by chloroform permits the collection of 3.2 grams of product which are crystallized from an ethanol-hexane mixture; weight: 1.25 gram; yield: 35.5%.

Analysis: $C_{29}H_{41}FO_5S$: Calculated %: C, 66.89; H, 7.94; F, 3.65; S, 6.16; Found %: C, 67.19; H, 8.14; F, 3.70; S, 6.22. Physical characteristics: F = 145°–150° C.; $[\alpha]_D^{20} = +82°$, (dioxanne: c = 1.4%); $\lambda$max. (methanol) at 236.5 nm, log.$_{10}$ $\epsilon$ = 4.294; Main absorptions of infra-red spectrum (KBr pellet): 1710, 1660, 1610, 1455, 1140, 980, 950, 930, 900 and 710 cm$^{-1}$.

EXAMPLE 6

Dihydroxy-11$\beta$, 17$\alpha$ thiol-21 dioxo-3,20 fluoro-9$\alpha$ methyl-16$\alpha$ pregnadiene-1,4-21 p. fluoro benzoate (JO 1013)

The reaction is carried out according to Example 4, starting from 13.68 grams of S-p.fluoro-thiobenzoic acid (87.6 mmols), 24.4 cu.cm. of sodium methylate solution 3.6. M (87.6 mmols) and 3.4 grams of Dihydroxy-11$\beta$, 17$\alpha$ iodo-21 dioxo-3,20 fluoro-9$\alpha$ methyl-16$\alpha$ pregnadiene-1,4 (6.76 mmols).

After reaction and evaporation of the solvents, the residue is treated with 800 cu.cm. of water and the insoluble is filtered and dried under vacuum - weight: 4.6 grams.

The crude product is purified by column chromatography on Florisil 60 – 100 mesh (80 grams). Elution by hexane and then by benzene eliminates the coloured products, and then elution by a benzene-chloroform mixture 1–3 (v/v) gives 0.9 grams of residue which is crystallized from an ethanol-hexane mixture. Weight: 0.45 gram; yield: 12.5%.

Analysis: $C_{29}H_{32}F_2O_5S$: Calculated %: C, 65.64; H, 6.08; F, 7.16; S, 6.04; Found %: C, 65.33; H, 6.24; F, 7.04; S, 5.92. Physical characteristics: F = 205°–210° C.; $[\alpha]_D^{20} = +265°$, (dioxanne c = 0.5%); $\lambda$max. (methanol at 236.5 nm, log.$_{10}$ $\epsilon$ = 4.516; Main absorptions of infra-red spectrum (KBr pellet): 1720, 1660, 1598, 1500, 1220, 1200, 1160, 920, 890, 840, 725 and 620 cm$^{-1}$.

EXAMPLE 7

Dihydroxy-11$\beta$, 17$\alpha$ thio-21 dioxo-3,20 pregnene-4-21 pivalate (JO. 1016).

In a reactor of 50 liters equipped as in Example 1, sodium S-thiopivalate is prepared from 100 grams of S-thiopivalic acid (0.844 mol), 214 cu.cm. of solution of sodium methylate, 3.95 M (0.844 mol.) in 25 liters of anhydrous acetone.

There are then added 285 grams (0.603 mol.) of Dihydroxy-11$\beta$, 17$\alpha$ iodo-21 dioxo-3,20 pregnene-4 and the mixture is brought up to the acetone reflux for two hours. The solvent is eliminated by distillation under vacuum until there is obtained a syrupy residue which is poured into 10 liters of iced water. The insoluble part is filtered and dried under vacuum.

The crude product is purified by recrystallization from ethanol; weight: 250 grams; yield: 89.5%.

Analysis: $C_{26}H_{38}O_5S$: Calculated %: C, 67.50; H, 8.28; S, 6.99; Found %: C, 67.60; H, 8.16; S, 7.09. Physical characteristics: F = 195°–200° C; $[\alpha]_D^{20} = +145°$, (dioxanne: c = 1%); $\lambda$max. (methanol) at 229 nm, log.$_{10}$ $\epsilon$ = 4.259; Main absorptions of infra-red spectrum (KBr pellet): 1722, 1688, 1660, 1623, 1368, 1237, 1116, 1038, 868 and 720 cm$^{-1}$.

EXAMPLE 8

Dihydroxy-11β, 17α thiol-21 dioxo-3,20 pregnene-4-21 heptanoate (JO 1027)

The reaction is carried out as described for Example 7, from 13.22 grams of S-heptanethioic acid (90 mmols) and 22.8 cu.cm. of sodium methylate solution (89 mmols) on the one hand and 30 grams of Dihydroxy-11β, 17α iodo-21 dioxo-3,20 pregnene-4 (63.5 mmols) on the other hand.

The crude product is isolated by the usual method and purified by column chromatography on 300 grams of Florisil (60–100 mesh). After elution with benzene which enables the by-products to be eliminated, elution by chloroform gives 22.4 grams of product which are crystallized from ethanol-hexane mixture, weight: 13.6 grams; yield = 43.6%. Analysis: $C_{28}H_{42}O_5S$: Calculated: C, 68.53; H, 8.63; S, 6.53; Found %; C, 68.66; H, 8.47; S, 6.44. Physical characteristics: F = 118° C. $[\alpha]_D^{20} = +135°$, (dioxanne; c = 1, 2%) λmax. (methanol) at 237.5 nm, $\log_{10} \epsilon = 4.287$; Main absorptions of infra-red spectrum (KBr pellet): 1728, 1692, 1640, 1605, 1360, 1225, 1122, 1035, 868 and 712 cm$^{-1}$.

EXAMPLE 9

Dihydroxy-11β, 17α thiol-21 dioxo-3,20 pregnene-4-21 p. fluoro-benzoate (JO 1026)

Carrying out the operation under the same conditions as in Example 7, from 42 grams of S-m.fluoro-thio-benzoic acid (0.269 mol.), 73.5 cu.cm. of sodium methylate solution 3.66 M (0.269 mol) and 72 grams of Dihydroxy-11β, 17α iodo-21-dioxo-3,20 pregnene-4 (0.153 mol), there are obtained after treatment and crystallization from methanol 22 grams of pale pink crystals. Yield = 28.8%.

Analysis: $C_{28}H_{33}FO_5S$: Calculated %: C, 67.17; H, 6.64; F, 3.80; S, 6.41; Found %: C, 67.31; H, 6.34; F, 3.73; S, 6.48. Physical characteristics: F = 225°–230° C $[\alpha]_D^{20} + 165°$, (dioxanne; c = 1,2 %) λmax. (methanol) at 236.5 nm, $\log_{10} \epsilon = 4.516$ Main absorptions of infra-red spectrum (KBr pellet): 1717, 1670, 1635, 1600, 1508, 1235, 1210, 1115, 920, 848 720 and 620 cm$^{-1}$.

EXAMPLE 10

Hydroxy-17α thiol-21 trioxo-3,11,20 pregnadiene-1,4-21 pivalate (JO 1032).

In a 250 cu.cm three necked round bottomed flask equipped with a mechanical stirrer, a dropping funnel and a calcium chloride tube, there are introduced 52 cu. cm. of anhydrous acetone and 2.81 grams of S-thiopivalic acid (23.8 mmols).

5.1 cu. cm. of methanol solution of sodium methylate 3.9 M (19.8 mmols) are introduced drop by drop in three minutes. The reaction medium is left for 15 minutes while stirring.

In the other hand, in a balloon flask of 1 liter fitted with a mechanical stirrer, a dropping funnel, a thermometer and a reflux condenser protected from moisture by a calcium chloride tube, 630 cu. cm. of anhydrous acetone and 6.3 grams (13.5 mmols) of hydroxy-17αiodo-21 trioxo-3,11,20 pregnadiene-1,4 are introduced.

After 15 minutes stirring at the laboratory temperature, a yellow solution is obtained into which there is introduced the acetone solution of sodium S-thiopivalate prepared above. The introduction is effected drop by drop in 15 minutes without variation of temperature.

The reaction medium is brought up to the reflux of the acetone for 2 hours, and the solvent is then eliminated by distillation under vacuum.

The solid yellow residue obtained is scrapped in 200 cu.m. of distilled water, filtered and dried under vacuum at 40° C. - weight 5.75 grams.

The product is purified by crystallization from 750 cu. cm. of methanol. After cooling, the yellow precipitate is filtered and dried under vacuum at 40° C; weight = 3.5 grams; yield = 56.3 %.

Analysis: $C_{26}H_{34}O_5S$: Calculated %: C, 68.09; H, 7.47; S, 6.99; Found %: C, 67.95; H, 7.53; S, 6.92. Physicals characteristics: F = 237°–240° C $[\alpha]_D^{20} = +182.5°$, (dioxanne; c = 1%) λmax. (methanol) at 235 nm, $\log_{10} \epsilon = 4.247$ Main absorptions of infra-red spectrum (KBr pallet) 1705, 1655, 1610, 1365, 1045, 960, 895, 810 and 700 cm$^{-1}$.

EXAMPLE 11

Hydroxy-17α Thiol-21 Trioxo-3,11,20 pregnadiene-1,4-21 heptanoate (JO 1033)

The sodium S-heptane-thioate is prepared in the usual manner from 8.58 grams (58.7 mmols) of S-heptanethioic acid, 12.5 cu.cm. of methanol solution of sodium methylate 3.9 M (49 mmols) in 100 cu. cm. of anhydrous acetone.

The acetone solution is introduced into a solution of 15.6 grams (33.3 mmols) of hydroxy-17α iodo-21 trioxo-3, 11, 20 pregnadiene-1,4 in one liter of acetone.

The reaction and the treatment are carried out following the usual method. The crude product obtained is purified by crystallization from an ethanol-petroleum ether mixture; weight à 4.5 grams; yield à 27.6%.

Analysis: $C_{28}H_{40}O_5S$: Calculated %: C, 69.10; H, 7.87; S, 6.59; Found %: C, 69.25; H, 7.95; S, 6.47. Physical characteristics: F inst. = 150°–151° C. $[\alpha]_D^{20} = +170°$; (dioxanne; c = 1%). λmax. (methanol) at 232 nm, $\log_{10} \epsilon = 4.3475$ Main absorptions of infra-red spectrum (KBr pellet): 1700, 1655, 1610, 1370, 1305, 1240, 1045, 895 and 700 cm$^{-1}$.

EXAMPLE 12

Hydroxy-17α thiol-21 trioxo-3,11,20 pregnene-4, 21-pivalate (JO 1034)

The sodium S-thiopivalate is prepared in the usual manner from 2.21 grams (18.7 mmols) of S-thiopivalic acid, 4.8 cu. cm of methanol solution of sodium methylate 3.9 M (18.7 mmols) of anhydrous acetone.

The solution is introduced into an acetone solution of hydroxy-17α iodo-21 trioxo-3,11,20 pregnene-4 (13.4 mmols).

After reaction and treatments, the product is purified by crystallization from 300 cu. cm. of methanol; weight à 3.25 grams; yield = 53%.

Analysis: $C_{26}H_{36}O_5S$: Calculated %: 67.79; H, 7.88; S, 6.96; Found %: C, 67.93; H, 7.69; S, 6.78. Physical characteristics: F = 213°–215° C $[\alpha]_D^{20} = +187.5°$, (dioxanne; c = 1%); max. (methanol) at 235 nm, $\log_{10} = 4.307$; Main absorptions of infra-red spectrum (KBr pellet) 1700, 1675, 1650, 1365, 1230, 955 and 870 cm$^{-1}$.

EXAMPLE 13

Hydroxy-17α thiol-21 trioxo-3,11,20 pregnene-4-21 heptanoate (JO 1035)

Under the same conditions as in the preceding example, from 8.25 grams (56.5 mmols) of S-heptanethioic acid and 14.5 cu. cm. of methanol solution of sodium methylate 3.9 M (56.5 mmols) on the one hand and 19 grams (4..4 mmols) of hydroxy-17αiodo-21 trioxo-3,11,20 pregnene-4 on the other hand, there is obtained a crude product which is purified by crystallization from 100 ml of methanol: weight: 12.6 grams; yield: 63.9%.

Analysis: $C_{28}H_{40}O_5S$: Calculated %: C, 68.82; H, 8.25; S, 6.56; Found %: C, 68.98; H, 8.31; S, 6.47. Physical characteristics: F = 125°–126° C. $[\alpha]_D^{20} = +175°$; (dioxanne; c = 1%); max. (methanol) at 234 nm, $\log_{10} = 4.286$; Main absorptions of infra-red spectrum (KBr pellet) 1700, 1655, 1275, 1050, 935 and 865 $cm^{-1}$.

There will now be described the tests which have enabled the determination of the pharmaco-dynamic properties of the esters of the 21-thiol steroids according to the invention.

ANTI-INFLAMMATORY ACTIVITY

The experimental local anti-inflammatory activity of the compounds presented was estimated in rats by their anti-proliferative (anti-granulomatous) action, and for certain of these, by their anti-arthritic activity and their anti-exudative activity.

(a) Anti-proliferative activity penicillin G and streptomycin

The anti-proliferative (anti-granulomatous) activity has been brought into evidence by means of a test, the principle of which is as follows.

The introduction of a foreign body into an organism produces a set of inflammatory reactions which results, in the chromic stage, in the formation of a defence granuloma around the foreign body. The proliferation of this granuloma is eliminated or attenuated by anti-inflammatory agents.

The technique employed is very similar to that described by Winter and Porter (J. Am. Pharm. Ass. 46/9. 515) 1957 with rats.

Homogeneous groups of 6 male adult rats of the Wistar Strain were used, distributed at random and having weights comprised between 180 and 200 grams.

The implants or pellets were prepared from rolls of dental cotton; the weight of the pellets was between 35 and 40 mg.

The products to be tested were dissolved in dimethylsulphoxide (DMSO) and the solutions obtained, deposited on the pellets at a volume of 0.2 ml per pellet. The DMSO was then evaporated under high vacuum at ambient temperature, the complete elimination of the solvent being checked by weighing the pellets. "Reference" pellets, soaked with the solvent alone, were treated in the same manner.

Immediately before their introduction, the pellets were soaked with an antibiotic solution (0.1 ml. of a solution of penicillin G and streptomycin containing 200.000 UI of penicillin G and 0.1 gram of streptomycin sulphate per cc.).

Each animal received two pellets in the sub-cutaneous dorsal tissue on each side of the spinal column, at the costo-lumbar angle, under light anaesthesia with ether. The day of the operation and for three days after, the animals received by sub-cutaneous injection, 0.1 ml. of the antibiotic solution in the caudal region.

Six days after the introduction, the animals were killed by inhalation of chloroform and the granulomae were extracted and weighed, (fresh weight), and then the initial weights of the cotton pellets were subtracted from the total weight.

Certain non-sulphured steroids causing a large increase in protein catabolism which can influence the formation of the granuloma independently of their anti-inflammatory action, the weights of the granulomae were expressed as a percentage of the body weight (technique proposed by G. Dipasquale and A. Meli: J. Pharm. Pharmacol. (1965), 17,367–382) and the anti-proliferative effect of the various compounds as a percentage inhibition with respect to the reference granulomae. The $DE_{50}$ were calculated by transferring the results on to semi-logarithmic paper.

(b) Anti-exudative action

The anti-exudative activity was brought into evidence by means of a test, the principle of which is as follows.

This test consists of creating, under the dorsal skin of the rat an air pouch in which an irritant product is injected. An inflammatory reaction appears rapidly and is shown by the accumulation of liquid in the pouch of air.

The introduction of an anti-inflammatory product into the air pouch reduced, more or less completely, the accumulation of exudate.

This study was carried out with male rats of the Wistar strain, the initial weight of which was between 160 and 180 grams, following the technique described by M. Fukuhara and S. Tsurufuji (Bio-Chem. Pharmac. 18, 475–484, 1969). Each lot comprised 10 animals distributed at random.

Twenty-four hours before the beginning of the test, each animal received a sub-cutaneous injection of 6 ml. of air in the dorsal region, previously shaved.

The following day, there was injected 4 ml. of a 2% carrageenan solution in the physiological solution (NaCl at 0.9 %), were injected in the pouch, the solution being kept lukewarm to prevent setting in a lump.

An injection of 0.1 ml. of a solution of penicillin and streptomycin containing 200,000 UI of penicillin and 0.1 gram of streptomycin per ml. was carried out immediately afterwards in the caudal region by sub-cutaneous methods.

Ninety-six hours after the administration of the carrageenan; the products under study were injected into the pouch in a volume of 0.2 ml. in suspension in carboxymethyl-cellulose at 0.5%.

Ninety-six hours after this last injection, the animals were killed and the exudate contained in the pouch was collected through a small incision made with a scalpel, and its volume was measured in a test tube.

The difference in volume of the exudate between the animals treated and the reference lot was expressed as a percentage inhibition. The $ED_{50}$ were determined by transferring these results on to semi-logarithmic paper.

(c) Anti-arthritic activity

The anti-arthritic activity was brought out by means of a test, the principle of which is as follows:

This test was carried out following a method derived from that described by Foldi-Borcsok and Coll. (Arzneimittel Forschung 21, 2025–2030, 1971).

The injection of kaolin in the tibioemetatarsal joint of the rat causes an inflammation which develops in two successive phases:
- an acute phase characterized by an oedema of the joint;
- a chronic phase which follows, characterized by the proliferation of an inflammatory granuloma.

The intensity of the inflammatory reaction is estimated following the width of the articulation.

Male rats of Wistar stock were utilized, the initial weight of which was between 180 and 200 grams. Each group comprised ten animals taken at random, in which the width of the right-paw tibio-metatarsal joint was measured to the nearest 1/20th of a millimeter.

All the animals received 0.05 ml. of suspension of kaolin at 10% in a 0.9% physiological solution by intra-articular injection in the right-paw tibio-metatarsal joint.

Eighteen hours after this injection, the width of the joint was measured (initial inflammation) and there was then carried out an intra-articular injection of the products under study, in suspension in 5% carboxy-methyl-cellulose at a volume of 0.05 ml. The animals belonging to the reference lot received 0.05 ml. of the vehicle by the same method.

Twenty-four hours after this last injection, the width of the joint treated was again measured and then daily for 9 or 10 days, according to the evolution of the animals of the reference group.

The variations of width of the joints treated, representing the anti-arthritic activity of the products under study, were expressed as a percentage of the initial inflammation according to the formula:

$$\text{Anti-arthritic activity on the } N\text{th day} = \frac{\Delta_1 - \Delta_n}{\Delta_1} \times 100$$

in which
$\Delta_1$ = increase in width of the joint with respect to its initial width, during the initial inflammation;
$\Delta_n$ = increase in width of the joint with respect to its initial width, on the day considered.

The calculations were carried out by using the averages of the individual results of each lot.

SYSTEMIC EFFECTS

The systemic effects of the compounds according to the invention were evaluated through the intermediary of their thymolytic activity and for some of these, their possible influence on the glucidic metabolism, the hydro-mineral equilibrium, the weight increase, the endocrine glands and the genital tractus was examined and also a possible ulcerogenic effect.

(d) Thymolytic effect

The thymolytic effects have been examined by means of a test, the principle of which is as follows:

The repeated administration of a gluco-corticoid having a systemic activity causes an involution of the defence system of the organism, of which two organs belong to the reticulo-endothelial system, the spleen and the thymus, this latter being the most sensitive to this action, especially with young animals. The thymic involution is estimated by weighing.

The various products were injected daily by the oral or the sub-cutaneous route for four days, to young male rats of Wistar-strain, the initial weight of which was between 45 and 55 grams, distributed at random by groups of ten.

The products under study were administered at a volume of 0.2 ml. per animal for both methods, in suspension in:
- Carboxy-methyl-cellulose at 5% for sub-cutaneous injection;
- Gum arabic at 5% for the oral route.

The animals of the reference groups received the same volume of the corresponding vehicle.

Ninety-six hours after the first administration, the animals were killed, the thymus glands being taken and weighed immediately.

For each animal, the weight of the thymus has been brought to 100 grams of body weight. The thymolytic activity of the products under study was then expressed as a percentage of regression of the thymus with respect to the animals of the reference group and the $ED_{50}$ of each product tested was estimated by transferring the percentage inhibition obtained for each dose on semi-logarithmic paper.

Action on the glucidic metabolism

The action on the glucidic metabolism was investigated by means of a test, the principle of which is as follows:

Gluco-corticoid reduce the peripheral needs of the organism in glucose, they also increase the synthesis by the liver of glycogen (neo-glycogenesis). Their action on the glucidic metabolism is thus indicated:
(1) By an increase of glycemia;
(2) by a glycogenic overload on the liver and especially by the persistence of the hepatic shock of glycogen in the food-deprived animal, and treated with a glyco-corticoid by comparison with the non-treated animal.

For this study, Wistar male rats were used; the initial weight of which was between 150 and 160 grams, distributed at random in groups of 10.

The products studied were administered by the oral route in suspension in 5% gum arabic, under a volume of 0.5 ml. per 100 grams, the animals of the reference group receiving the same volume of vehicles under the same condition.

The treatments were carried out daily for four days, a fifth administration being given seven hours before killing the animals, which took place 96 hours after the first administration.

Eighteen hours before being killed, all the animals were put on a water diet, this period of fasting having proved sufficient to eliminate the hepatic stock of glycogen in the animals of the reference group.

Immediately after killing the animals, a sample of the hepatic tissue was taken from the central lobe and weighed. Immediately afterwards, it was subjected to digestion in 30% potassium hydroxide in a boiling water-bath for 20 minutes. The glycogen contained in the digestate was then dosed, following the technique described by R. O. Stafford, L. E. Barnes and Coll. (Proc. Soc. Exp. Med. 39/3, 371–374, 1955).

The content of glycogen in the liver samples has been expressed in grams of glycogen per 100 grams of hepatic tissue.

(f) Action on the hydro-mineral metabolism

The action on the hydro-mineral metabolism was examined by means of a test, the principle of which is as follows:

The gluco-corticoids are not all free from mineral-corticoid effects (for example hydro-cortisone). These latter are indicated by:

- A reduced renal elimination of sodium (sodium retention);
- a loss of potassium (potassium leakage), these two effects reproducing the action of aldosteron.

This study has been carried out on male Wistar rats having weights between 180 and 190 grams.

The animals were distributed at random in groups of ten.

The products under study were administered by the oral route in suspension in 5% gum arabic. The animals of the reference group received the same volume of vehicle under the same conditions.

The treatments were carried out daily for 4 days.

The renal functional exploratory test was effected 90 hours after the first administration of the product tested.

Eighteen hours before the test, the animals were completely deprived of food and water, this being subsequently maintained up to the end of the test.

Immediately before the renal functional test, the animals received an overdose by the oral route of physiological solution equal to 5% by volume of their body weight.

The urine passed during five hours was collected for each animal in a polyethylene tube.

The concentration of sodium was determined in each sample by flame photometry; the total quantitt excreted was then calculated as a function of the corresponding volume of urine. The values obtained for each group were then compared following the Fisher Student method with the quantity of sodium excreted by the animals of the reference group.

(g) Action on the protein metabolism

The action on the protein metabolism was examined by means of a test, the principle of which is as follows:

The administration of gluco-corticoids results in a disturbance of the protein metabolism, which is shown by an exaggerated protein catabolism resulting in shrinking of the tissues objectified by an inhibition of growth in weight in the young animal and a loss of body weight in the adult animal.

For this study, immature rats of Wistar strain were utilized, the initial weight of which was between 45 and 55 grams, which were distributed at random groups of 10.

The products under study were administered daily for 4 days. The animals were weighed daily during the 4 days of treatment and 24 hours after the last dose.

The products tested were administered either orally or by sub-cutaneous injection, in suspension in 5% gum arabic for the oral route or in carboxy-methyl-cellulose at 5% for the sub-cutaneous method, the animals of the reference group receiving the same volume of vehicle by the same method as the corresponding animals treated.

The average variation of the body weight during the 96 hours treatment was calculated for each group of animals.

(h) Long-term administration

The action on the endocrine glands and the genital tractus, and a possible ulcerogenic effect were investigated, together with the effects on the glucidic and proteic metabolisms, on the hydro-mineral equilibrium after long-term administration.

The principle of the tests employed is as follows.

The repeated administration of corticoids may result in an inhibition of the secretion of the ante-hypophysiary hormone which is shown by a lowering of the effectiveness of the target-glands (example: adrenal-glandes) and indirectly of certain organs which are under the dependence of a hormone secretion (example: genital tractus). Certain corticosteroids also possess in addition an action which increases virility or feminity, capable of causing animalies of the reproductive functions.

The ulcer-producing action of certain corticoids, after repeated administration is well known, but the mechanism of this action still remains doubtful.

These studies have been carried out for some of the products according to the invention after sub-chronic administration.

There were utilized groups of 10 male rats and ten female rats of Sprague-Dawley S.P.F. strain which have been given the products under study by sub-cateneous methods daily for four weeks.

The products were administered in suspension in 5% carboxy-methyl-cellulose under a volume of 0.5 ml. per 100 grams of body weight, in three different doses, the animals of the reference lot receiving the same volume of the vehicle alone.

At the end of this study there were extracted:
(1) the adrenal glandes;
(2) the gonads (testicles or ovaries);
(3) the seminal vesicles or the uterine tubes;
(4) the stomach;
(5) the duodenum;
(6) certain portions of the small intestine, of the ileum and of the colon.

The samples numbered (1), (2) and (3) were immediately weighed. All the samples were then fixed for histological examination in the Bouin-Holland fixator.

In order to confirm certain previous results of the pharmacological short-term study, there has furthermore been determined, for each lot of animals:

The evolution of weight and the consumption of food during the treatment;
at the end of the treatment:
the glycemia,
the serum ionogram,
the sodium excretion in 5 hours

RESULTS OF THE PHARMACOLOGICAL STUDY

There will now be described the results of the pharmacological study.

(1) Anti-proliferative activity

The $ED_{50}$ obtained for each of the products presented and the corresponding base steroids are indicated in Tables I, II and III below.

TABLE I

| Derivatives of dexamethasone | |
|---|---|
| Dexamethasone (base) : | $ED_{50} = 1$ mg/pellet |
| Dexamethasone (acetate) : | $ED_{50} = 0.4$ mg/pellet |

TABLE I-continued

| Derivatives of dexamethasone | |
| --- | --- |
| JO 1008 | $ED_{50} = 1$ mg/pellet |
| JO 1010 | $ED_{50} = 0.5$ mg/pellet |
| JO 1013 | $ED_{50} = 0.5$ mg/pellet |

TABLE II

| Derivatives of prednisolone | |
| --- | --- |
| Prednisolone (base) : | $ED_{50} = 4$ mg/pellet |
| Prednisolone (acetate) : | $ED_{50} = 2$ mg/pellet |
| JO 1007 | $ED_{50} = 0.44$ mg/pellet |
| JO 1009 | $ED_{50} = 0.5$ mg/pellet |
| JO 1014 | $ED_{50} = 0.5$ mg/pellet |

TABLEAU III

| Derivatives of hydro-cortisone | |
| --- | --- |
| Hydrocortisone (base) : | $ED_{50} = 10$ mg/pellet |
| Hydrocortisone (acetate) : | $ED_{50} = 1.05$ mg/pellet |
| JO 1016 | $ED_{50} = 0.35$ mg/pellet |
| JO 1026 | $ED_{50} = 0.4$ mg/pellet |

(2) Thymolytic activity

The $ED_{50}$ obtained for each of the products presented and for the corresponding basic steroids are indicated in Tables IV, V, VI which follow: ($ED_{50}$ calculated from the total doses administered during four days per rat of about 50 grams).

TABLE IV

| Derivatives of dexamethasone | Oral route | Sub-cutaneous route |
| --- | --- | --- |
| Dexamethasone (base) : | 0.013 mg | 10.02 mg |
| Dexamethasone acetate) : | 0.01 mg | 0.009 mg |
| JO 1008 | — | 0.8 mg |
| JO 1010 | — | 0.4 mg |
| JO 1013 | — | 0.8 mg |

TABLE V

| Derivatives of prednisolone | Oral route | Sub-cutaneous route |
| --- | --- | --- |
| Prednisolone (base) : | 0.34 mg | 0.84 mg |
| Prednisolone (acetate) : | 0.64 mg | 0.23 mg |
| JO 1007 | 9.6 mg | 30.4 mg |
| JO 1009 | — | 8 mg |
| JO 1014 | 40 mg | >40 mg |

TABLE VI

| Derivatives of hydrocortisone | Oral route | Sub-cutaneous route |
| --- | --- | --- |
| Hydrocortisone (base) : | 4 mg | 1.8 mg |
| Hydrocortisone (acetate) : | 4 mg | 0.68 mg |
| JO 1016 | 400 mg | >120 mg |
| JO 1026 | >40 mg | >40 mg |

(3) Ratio of the local anti-inflammatory activity to the Thymolytic activity

The ratio of the local anti-inflammatory activity to the thymolytic activity is all the greater as these products possess a low anti-inflammatory activity ($ED_{50}$ high in the numerator) and a large thymolytic activity ($ED_{50}$ low in the denominator).

The ratio is indicated in Tables VII, VIII and IX which follow:

TABLE VII

| Derivatives of the dexamethasone | | |
| --- | --- | --- |
| | $\frac{ED_{50} \text{ anti-proliferative activity}}{ED_{50} \text{ Thymolytic activity}}$ | |
| | Thymolytic activity determined by the oral route | Thymolytic activity determined by subcutaneous route |
| Dexamethasone (base) : | 80 | 50 |
| Dexamethasone (acetate) : | 40 | 40 |
| JO 1008 | — | 1.25 |
| JO 1010 | — | 1.25 |
| JO 1013 | — | 0.625 |

TABLE VIII

| Derivatives of the prednisolone | | |
| --- | --- | --- |
| | $\frac{ED_{50} \text{ Anti-proliferative activity}}{ED_{50} \text{ thymolytic activity}}$ | |
| | Thymolytic activity determined by the oral route | Thymolytic activity determined by subcutaneous route |
| Prednisolone (base) : | 12.5 | 5 |
| Prednisolone (acetate) : | 3 | 9 |
| JO 1007 | 0.046 | 0.014 |
| JO 1009 | — | 0.0625 |
| JO 1014 | 0,012 | 0.0125 |

TABLEAU IX

| Derivatives of hydrocortisone | | |
| --- | --- | --- |
| | $\frac{ED_{50} \text{ Anti-proliferative activity}}{ED_{50} \text{ Thymolytic activity}}$ | |
| | Thymolytic activity determined by the oral route | Thymolytic activity determined by the subcutaneous route |
| Hydrocortisone (base) | 2.5 | 5.5 |
| Hydrocortisone (acetate) | 0.25 | 1.2 |
| JO 1016 | <0.003 | 0.0008 |
| JO 1026 | <0.01 | <0.01 |

(4) Anti-exudatory activity

The results indicated on Table X were obtained with the JO 1016.

TABLE X

| | Anti-exudatory activity |
| --- | --- |
| Hydrocortisone acetate | $ED_{50} = 1,5$ mg |
| JO 1016 | $ED_{50} = 1.5$ mg |

(5) Anti-arthritic activity

For example, the results obtained are referred to:

a derivative of dexamethasone : JO 1008;
a derivative of prednisolone : JO 1007;
a derivative of hydrocortisone : JO 1016,
and also to the corresponding reference steroids.

The figures indicated in Table XI below represent the anti-arthritic activity of the products, estimated from the diminution in width of the joint (as a percentage of the initial inflammation), 24 hours after their injection and 120 hours after the injection.

The various products and the corresponding reference steroids were administered in a ratio of doses equal to the ratio of their respective molecular weights.

TABLE XI

|  | Dose | 24 hours | 120 hours |
| --- | --- | --- | --- |
| Dexamethasone base | 0.1 mg | − 78.8 % | − 51.3 % |
| JO 1008 | 0.126 mg | − 64.7 % | − 90.8% |
| Prednisolone base | 1 mg | − 57.7 % | − 1.9 % |
| JO 1007 | 1,278 mg | − 62.4 % | − 77,3 % |
| Hydrocortisone acetate | 2.91 mg | − 65.0 % | − 76.2 % |
| JO 1016 | 3.34 mg | − 58.9 % | − 81.2 % |

(6) Effect on the glucidic and proteic metabolisms, the hydromineral equilibrium, the endocrine glands and the genital tractus; examination for ulcerogenic and pro-infectious effects.

There are presented by way of example, the results obtained with one of the products presented, the JO 1016, in comparison with the corresponding reference steroid: hydro-cortisone acetate.

The results concerning the effects of the product according to the invention on the glucidic and proteic metabolisms and the hydro-mineral equilibrium, corresponding:

On the one hand to the short term study (96 hours) following the procedures described in paragraphs e), f) and g), On the other hand to the long term study (daily administration for 4 weeks following the procedure described in paragraph h).

During the course of the long-term study, the JO 1016 was administered daily to the male and female rats in doses of 100 mg/kg, 250 mg/kg, 500 mg/kg by the sub-cutaneous route. Comparatively, a similar study was undertaken with hydrocortisone acetate which was administered in doses of 218 mg/kg and 436 mg/kg (doses calculated from the ratio of molecular weights between the JO 1016 and hydro-cortisone acetate) to the male rat by the same method: this study had to be broken-off on the 14th day due to the high mortality observed with the strong dose.

Ulcer-producing and pro-infectious effect (see procedure h).

The organs of the surviving animals were examined: the result of these macroscopic observations is indicated in Table XII

TABLE XII

| | | 14 days of treatment with hydrocortisone acetate | | 4 weeks of treatment with JO 1016 | |
| --- | --- | --- | --- | --- | --- |
| | | Doses | | Doses | |
| Organs examined | Macroscopic observation | 218 mg/kg Case No | 436 mg/kg Case No | 250 mg/kg Case No | 500 mg/kg Case No |
| LIVER | Presence of abscess | 7/8 | 1/2 | 0/10 | 0/10 |
| KIDNEYS | " | 2/8 | 1/2 | 0/10 | 0/10 |
| SPLEEN | Atrophied | 8/8 | 2/2 | 0/10 | 0/10 |
| THYMUS | Atrophied | 8/8 | 2/2 | 0/10 | 0/10 |
| STOMACH | Ulcerated | 6/8 | 2/2 | 0/10 | 0/10 |
| | Ulcerated and infected | 4/8 | 2/2 | 0/10 | 0/10 |

Action on the glucidic metabolism

Table XIII which follows indicates the content of glycogen in the liver with the reference animals and the treated animals for 96 hours after a water diet of 18 hours (see procedure (e)).

TABLE XIII

| | | Glycogen in g/100 g of hepatic tissue |
| --- | --- | --- |
| References | | 0.15 |
| Hydrocortisone acetate | 2 mg/kg | 0.19 |
| Hydrocortisone acetate | 5 mg/kg | 0.45 |
| Hydrocortisone acetate | 10 mg/kg | 0.46 |
| Hydrocortisone acetate | 20 mg/kg | 1.26 |
| Hydrocortisone acetate | 50 mg/kg | 2.49 |
| JO 1016 | 25 mg/kg | 0.25 |
| JO 1016 | 50 mg/kg | 0.39 |
| JO 1016 | 100 mg/kg | 0.42 |

Proportions of glycemia

The following Tables XIV and XV indicate the results of the proportions of glycemia with the reference animals and animals treated for 4 weeks following the procedure (h)

TABLE XIV

| Male animals | Average (g/liter) ± standard error | No of animals | Percentage of variation and probabilities |
| --- | --- | --- | --- |
| Reference group | 1.1 ± 0,05 | 10 | |
| JO 1016-100 mg/kg | 1.2 ± 0.04 | 10 | + 16 % $p < 0.01$ |
| JO 1016-250 mg/kg | 1.2 ± 0.05 | 10 | + 15 % $0.02 < p < 0.05$ |

TABLE XIV-continued

| Male animals | Average (g/liter) ± standard error | No of animals | Percentage of variation and probabilities |
|---|---|---|---|
| JO 1016-500 mg/kg | 1,1 ± 0.03 | 10 | N.S. |

TABLE XV

| Female animals | Average (g/liter) ± standard error | Number of Animals | Percentage of Variation and possibilities |
|---|---|---|---|
| Reference group | 1,00 ± 0,04 | 10 | |
| JO 1016-100 mg/kg | 1.10 ± 0,04 | 10 | + 10 % N.S. |
| JO 1016-250 mg/kg | 1.21 ± 0,03 | 10 | + 21 % p < 0.01 |
| JO 1016-500 mg/kg | 1,10 ± 0,04 | 10 | + 10 % N.S. |

Hydro-mineral equilibrium

The results obtained with hydro-cortisone acetate and the JO 1016 in the case of a treatment lasting 96 hours following the procedure (f) are indicated in the following Table XVI.

TABLE XVI

| | Meq of sodium excreted Average ± standard error | Number of animals | Percentage of variation and probabilities |
|---|---|---|---|
| Reference group | 0.816 ± 0.0493 | 4 | |
| Hydrocortisone acetate- 16 mg/kg | 0,371 ± 0,0827 | 5 | − 55 % 0,001 < p < 0,01 |
| JO 1016 16 mg/kg | 0.820 ± 0.1040 | 5 | 0,4 % N.S. |
| JO 1016 32 mg/kg | 0.754 ± 0.0465 | 4 | − 8 % N.S. |
| JO 1016 80 mg/kg | 0.684 ± 0.1591 | 4 | − 16 % N.S. |
| JO 1016 160 mg/kg | 0.664 ± 0.0484 | 5 | − 19 % N.S. |

The result obtained in the case of a treatment lasting 4 weeks following the procedure (h) are indicated in the following Table XVII.

TABLE XVII

| | Meq of sodium excreted Average ± standard error | Number of animals | Percentage of variation and probabilities |
|---|---|---|---|
| Reference group male rat | 1.77 ± 0.089 | 10 | — |
| Reference group female rat | 1.17 ± 0.065 | 10 | — |
| JO 1016 male rat 500 mg/kg | 1,41 ± 0,116 | 10 | − 20 % 0.02 < p < 0,05 |
| JO 1016 female rat 500 mg/kg | 0,91 ± 0.98 | 10 | − 22 % 0,02 < p < 0.05 |

Proteic metabolism

The increase in weight of immature rats (45 to 55 grams) treated for 96 hours following the procedure (g) by JO 1016, by the oral or the sub-cutaneous routes (average weight at the end of the study, less the average weight at the beginning) are indicated in the following Table XVIII.

TABLE XVIII

| | Oral route | Sub-cutaneous route |
|---|---|---|
| References | 13 g | 14 g |
| JO 1016 1 mg/rat/day | — | 17 g |
| JO 1016 3 mg/rat/day | 14 g | — |
| JO 1016 10 mg/rat/day | 11 g | 16 g |
| JO 1016 30 mg/rat/day | 13 g | 16 g |
| JO 1016 10 mg/rat/day | 8 g | — |

The weights of the animals at the end of the 4 weeks of treatment by the sub-cutaneous route are indicated in the following Tables XIX and XX.

TABLE XIX

| Male rats | Average (g) ± standard error | Number of Animals | Percentages of variation and probabilities |
|---|---|---|---|
| References | 296 ± 7.6 | 10 | |
| JO 1016 100 mg/kg | 299 ± 45.2 | 10 | N.S. |
| JO 1016 250 mg/kg | 289 ± 7.7 | 10 | N.S. |
| JO 1016 500 mg/kg | 274 ± 2,5 | 10 | − 7 % 0.02 < p < 0.05 |

TABLE XX

| Female rats | Average (g) ± standard error | Number of animals | Percentages of variation and probabilities |
|---|---|---|---|
| References | 218 ± 3.22 | 10 | |
| JO 1016 100 mg/kg | 219 ± 3.06 | 10 | N.S. |
| JO 1016 250 mg/kg | 216 ± 3.18 | 10 | N.S. |
| JO 1016 500 mg/kg | 198 ± 4.85 | 10 | − 9 % 0.001 < p < 0.01 |

After 14 days of treatment by hydrocortisone at corresponding ratio, by the sub-cutaneous route, weights of the animals are indicated in the following Table XXI.

TABLE XXI

| Male rats | Average (g) ± standard error | Number of animal | Percentages of variation and probabilities |
|---|---|---|---|
| References | 264 ± 4.33 | 10 | |
| Hydrocortisone acetate 218 mg/kg | 110 ± 2.10 | 8 | −58.4 % 0,001<p <0.01 |
| Hydrocortisone acetate 436 mg/kg | 105 ± 4.12 | 2 | −60.2 % 0.001 <p <0.01 |

Action on the endocrine glands and the genital tractus

After a long-term treatment by the JO 1016, following the procedure (h), the average weights of the following organs: adrenal glandes, gonads, seminal vesicles, uterine tubes are indicated in the following Table XXII

TABLE XXII

| | References | JO 1016 | | |
| | | 100 mg/kg | 250 mg/kg | 500 mg/kg |
|---|---|---|---|---|
| Adrenal glandes (male rats) mg | 15.2 mg | 14.9 mg N.S. | 12,3 mg N.S. | 13.5 mg N.S. |
| Adrenal glandes (female rats) | 25,1 mg | 26.7 mg N.S. | 24,5 mg N.S. | 27,0 mg N.S. |
| Testicles | 1.131 mg | 1.143 g N.S. | 1.144 g N.S. | 1.207 g N.S. |
| Ovaries | 38.5 mg | 38.4 mg N.S. | 38.3 mg N.S. | 39.3 mg N.S. |
| Seminal vesicles | 284.3 mg | 328.0 mg N.S. | 296.0 mg N.S. | 274.6 mg N.S. |
| Uterine tubes | 150.4 mg N.S. | 211.8 mg N.S. | 184.7 mg N.S. | 165.4 mg N.S. |

(Weights expressed per 100 grams of body weight.)

The histological examination of these various organs has not furthermore brought into evidence any alteration of their structure:
- neither atrophy nor surrenal hypertrophy;
- nor modification of the functional aspect of the male and female genital organs.

POSOLOGY

The products described in the present invention are preferably utilized by local methods on the skin, the mucous membranes of the O.R.L. organ, the mucous membranes of the respiratory organs and the high and low digestive mucous.

The products are also used locally in the form of intra-articular injectable suspensions.

Generally speaking, the products are presented in the form of injectable, oral, nasal and auricular suspensions, of mouth-washes, gels and pomades, of suppositories, tablets and aerosols.

For the forms in which the product is in suspension, or may be considered as such, the active principle is utilized in the "micronized" form, the mean dimension of the particles being 2 microns.

The useful posology of the structures described by the present invention, as a function of their method of administration, extends between 0.25 and 50 mg. per unit taken and 1 to 200 mg. per day in adults animals.

The pharmaceutical forms may contain the products according to the invention, alone or associated with other therapeutic agents.

What we claim is:

1. As a new compound a hydrocortisone derivative of the general formula:

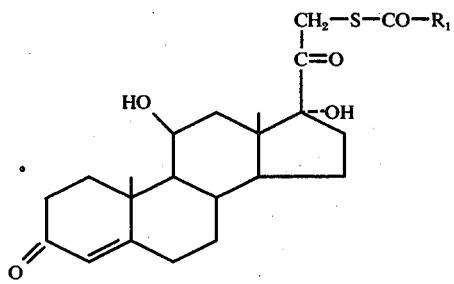

wherein:
R$_1$ is an alkyl radical having 4 or 6 carbon atoms or is the p-fluorophenyl radical.

2. The dihydroxy-11β,17αthio-21 dioxo-3,20-pregnene-4 21-pivalate.

3. The dihydroxy-11β,17αthio-21 dioxo-3,20-pregnene-4 21-heptanoate.

4. The dihydroxy-11β,17αthio-21 dioxo-3,20-pregnene-4 21-p-fluorobenzoate.

* * * * *

UNITED STATES PATENT AND TRADEMARK OFFICE
CERTIFICATE OF CORRECTION

PATENT NO. : 4,014,909
DATED : March 29, 1977
INVENTOR(S) : Dieran Robert Torossian, Gilbert Gustave Aubard and Jacky Marcel Gerard Legeai It is certified that error appears in the above-identified patent and that said Letters Patent are hereby corrected as shown below:

In column 3, line 55, delete [$R_1$, $R_2$, $R_3$, $R_{R5}$, $R_6$] and insert therefor $R_1$, $R_2$, $R_3$, $R_4$, $R_5$, $R_6$.

In column 4, line 36, after "log.$_{10}$" insert $\underline{C}$.

In column 5, line 45, before "92°" insert a plus sign $\underline{+}$.

In column 7, line 40, before "+165°" insert an equals sign $\underline{=}$.

In column 8, line 61, before "67.79 insert $\underline{C}$.

In column 20, line 26, Table XIX, under the column headed "Average (g) ± standard error", delete [299±45.2] and insert therefor $\underline{299 \pm 5.2}$.

Signed and Sealed this

Twenty-eighth Day of June 1977

[SEAL]

Attest:

RUTH C. MASON
*Attesting Officer*

C. MARSHALL DANN
*Commissioner of Patents and Trademarks*

UNITED STATES PATENT AND TRADEMARK OFFICE
CERTIFICATE OF CORRECTION

PATENT NO. : 4,014,909
DATED : March 29, 1977
INVENTOR(S) : Dieran Robert Torossian, Gilbert Gustave Aubard and Jacky Marcel Gerard Legeai It is certified that error appears in the above-identified patent and that said Letters Patent are hereby corrected as shown below:

On the first page, under the heading "Foreign Application Priority Data" please correct same to read:

May 30, 1973    France    73.19734

Signed and Sealed this

Twentieth Day of December 1977

[SEAL]

Attest:

RUTH C. MASON
Attesting Officer

LUTRELLE F. PARKER
Acting Commissioner of Patents and Trademarks

UNITED STATES PATENT AND TRADEMARK OFFICE
CERTIFICATE OF CORRECTION

PATENT NO. : 4,014,909
DATED : March 29, 1977
INVENTOR(S) : Dieran Robert Torossian, Gilbert Gustave Aubard and Jacky Marcel Gerard-Legeai It is certified that error appears in the above-identified patent and that said Letters Patent are hereby corrected as shown below:

Column 5, EXAMPLE 3, correct the title of the example to read:

Dihydroxy-11$\beta$, 17$\alpha$ thiol-21 dioxo-3,20 pregnadiene-1,4-21 p. fluorobenzoate (JO 1014)

Signed and Sealed this

Seventh Day of March 1978

[SEAL]

Attest:

RUTH C. MASON
Attesting Officer

LUTRELLE F. PARKER
Acting Commissioner of Patents and Trademarks